US008940314B2

(12) United States Patent
Arimoto

(10) Patent No.: US 8,940,314 B2
(45) Date of Patent: Jan. 27, 2015

(54) REPELLENT TO INSECTS HARMFUL TO A PLANT AND METHOD FOR REPELLING THE SAME

(75) Inventor: Yutaka Arimoto, Wako (JP)

(73) Assignee: Riken, Wako-shi (JP)

(*) Notice: Subject to any disclaimer, the term of this patent is extended or adjusted under 35 U.S.C. 154(b) by 412 days.

(21) Appl. No.: 11/683,134

(22) Filed: Mar. 7, 2007

(65) Prior Publication Data

US 2007/0190096 A1    Aug. 16, 2007

Related U.S. Application Data

(63) Continuation of application No. PCT/JP2005/016513, filed on Sep. 8, 2005.

(30) Foreign Application Priority Data

Sep. 8, 2004    (JP) ................. 2004-260744

(51) Int. Cl.
A01N 37/06    (2006.01)
A01N 37/12    (2006.01)
A01N 25/30    (2006.01)
A01N 43/16    (2006.01)
A01N 43/08    (2006.01)

(52) U.S. Cl.
CPC ............... *A01N 43/08* (2013.01); *A01N 25/30* (2013.01); *A01N 37/06* (2013.01); *A01N 37/12* (2013.01); *A01N 43/16* (2013.01)
USPC ........... 424/405; 424/727; 424/755; 424/757; 514/25; 514/546; 514/547

(58) Field of Classification Search
None
See application file for complete search history.

(56) References Cited

U.S. PATENT DOCUMENTS

| 4,632,827 | A | * | 12/1986 | Schlosser et al. ............... 514/63 |
| 5,658,851 | A | | 8/1997 | Murphy et al. |
| 5,661,181 | A | | 8/1997 | Mutschler et al. |
| 5,863,909 | A | | 1/1999 | Kurita et al. |
| 6,001,874 | A | * | 12/1999 | Veierov ......................... 514/533 |
| 2001/0034368 | A1 | * | 10/2001 | Arimoto et al. ............... 514/552 |
| 2003/0049297 | A1 | | 3/2003 | Tomioka et al. |
| 2004/0142822 | A1 | | 7/2004 | Suzuki et al. |

FOREIGN PATENT DOCUMENTS

| JP | 49-102836 | 9/1974 |
| JP | 08-151302 | 6/1996 |
| JP | 08-325104 | 12/1996 |
| JP | 10-109908 A | 4/1998 |
| JP | 2001-122706 | 5/2001 |
| JP | 2002-265305 | 9/2002 |
| JP | 2005-41805 | 2/2005 |
| WO | WO 02/22753 | 3/2002 |

OTHER PUBLICATIONS

Extended Supplementary European Search Report issued on Jun. 14, 2011 in corresponding European Application No. 05 78 2286.
Database WPI, Week 199827, Thomson Scientific, London, GB; AN 1998-306067, XP 002639309, Apr. 28, 1998, 1 Page (Corresponds to JP 10-109908 A).
Database EPODOC[Online], European Patent Office, The Hague, NL; XP 002639310, Apr. 28, 1998, 2 Pages(Corresponds to JP 10-109908 A).
Database CA [Online], Chemical Abstracts Service, Columbus, Ohio, US; XP 002639311, Retrieved from STN-International Accession No. 129:13504, Jul. 7, 1998, 2 Pages (Corresponds to JP 10-109908 A).
Database CA [Online], Chemical Abstracts Service, Columbus, Ohio, US; XP 002639312, Retrieved from STN-International International Accession No. 136:195659, index terms "IT", Mar. 21, 2002, 1 Page.
Database WPI, Week 197526, Thomson Scientific, London, GB; AN 1975-43302W, XP 002639313, Sep. 28, 1974, 1 Page (Corresponds to JP 49-102836 A which was previously filed on Apr. 25, 2007).
Database CA [Online], Chemical Abstracts Service, Columbus, Ohio, US; XP 002639314, Retrieved from STN-International Accession No. 83:2351, May 12, 1984, 3 Page (Corresponds to JP 49-102836 A which was previously filed on Apr. 25, 2007).
Database Biosis [Online], Biosciences Information Service, Philadelphia, PA, US; 1997, J. A. Pickett et al., "Developing Sustainable Pest Control from Chemical Ecology", XP 002639315, Database accession No. PREV199799790601 and Agriculture Ecosystems and Environment, vol. 64, No. 2, 1997, 1 Page.
Database Biosis [Online], Biosciences Information Service, Philadelphia, PA, US; Jun. 2001, Annie Fenigstein et al., "Effects of Five Vegetable Oils on the Sweet Potato Whitefly Bemisia Tabaci", XP 002639316, Database Accession No. PREV200100366021 and Phytoparasitica, vol. 29, No. 3, Jun. 2001, 1 Page.
Database Biosis [Online], Biosciences Information Service, Philadelphia, PA, US; Dec. 2003, B. Martin Lopez et al., "Short Communication. Repellency and Toxicity of Oils from Different Origins on Myzus Persicae Sulzer (Homoptera: Aphididae) in Pepper", XP 002639317, Database Accession No. PREV200400212476 and Spanish Journal of Agricultural Research, vol. 1, No. 4, Dec. 2003, 1 Page.
Notice of Allowance issued Jan. 30, 2013 in Korean Patent Application No. 10-2007-7007929 (with English translation).

* cited by examiner

Primary Examiner — Kortney L Klinkel
(74) Attorney, Agent, or Firm — Oblon, Spivak, McClelland, Maier & Neustadt, L.L.P.

(57) ABSTRACT

The invention provides a repellent to harmful flying insects which comprises as an effective ingredient at least one selected from the group consisting of glycerin fatty acid ester, sorbitan fatty acid ester, acetylated monoglyceride, organic acid monoglyceride, propylene glycol fatty acid ester, polyoxyethylene sorbitan, fatty acid, sucrose fatty acid ester, sorbitan, and soybean oil fatty acid methyl ester; a method for repelling harmful flying insects which comprises the step of applying the repellent to a plant to which the insects are harmful.

13 Claims, No Drawings

REPELLENT TO INSECTS HARMFUL TO A PLANT AND METHOD FOR REPELLING THE SAME

CROSS-REFERENCE TO A RELATED APPLICATION

The present application is a continuation of International Application PCT/JP05/016513, filed Sep. 8, 2005, which claims priority to Japanese Application No. 2004-260744, filed Sep. 8, 2004.

FIELD OF THE INVENTION

This invention relates to a repellent to insects harmful to a plant and method for repelling the same

BACKGROUND ART

There are serious damages to agricultural products, fruit vegetables, fruit trees, flowers and ornamental plants caused by harmful insects such as white flies, aphids, thrips, etc. There have been proposed various means for controlling the insects including chemical control, biological control, physical control, etc. Chemicals include organic phosphorus agents, carbamates, synthetic pyrethroids, etc. However, if chemicals are used, in many cases, most insects acquire resistance to the chemicals and the effects are gradually decreased or totally lost. In addition, many chemicals are toxic to human and animals and it is difficult to use the chemicals in a large amount or frequently. Some biological or physical control means are effective but not fully satisfactory from the view point of cost, general-purpose properties, etc. (see non-patent document 1).

Accordingly, there are strong needs for means for controlling harmful insects with low cost, high general purpose properties, and high safety to human and animals.

Non-patent document 1: "Takeda Plant Disease Control Series, Vol. 9, February 1996, Topical harmful insects" published by Takeda Pharmaceutical Co., Ltd.

SUMMARY OF THE INVENTION

An object of the invention is to provide a repellent to insects harmful to a plant, in particular, harmful flying insects.

Another object of the invention is to provide a method for repelling insects harmful to a plant, in particular, harmful flying insects.

The invention provides a repellent to insects harmful to a plant and a method for repelling insects harmful to a plant as described below.

1. A repellent to harmful flying insects which comprises as an effective ingredient at least one member selected from the following compounds:
   glycerin fatty acid ester, sorbitan fatty acid ester, acetylated monoglyceride, organic acid monoglyceride, propylene glycol fatty acid ester, polyoxyethylene sorbitan, fatty acid, sucrose fatty acid ester, sorbitan, and soybean oil fatty acid methyl ester.
2. The repellent of the above item 1 wherein the effective ingredient is at least one member selected from the following compounds:
   glycerin monofatty acid ester, glycerin mono/difatty acid ester, sorbitan fatty acid ester, acetylated monoglyceride, organic acid monoglyceride, polyglycerin fatty acid ester, propylene glycol fatty acid ester, fats and oils, polyoxyethylene sorbitan, synthetic fats and oils, fatty acid, sucrose fatty acid ester, sorbitan, and soybean oil fatty acid ester.
3. The repellent of the above item 1 or 2 wherein the harmful flying insects are whiteflies.
4. The repellent of the above item 3 wherein the effective ingredient is at least one member selected from the following compounds:
   glycerin monocaprylate, glycerin mono-12-hydroxy stearate, glycerin monooleate, glycerin mono/dioleate, sorbitan laurate, sorbitan oleate, sorbitan trioleate, glycerin diacetomonolaurate, citric acid unsaturated fatty acid monoglyceride, succinic acid saturated fatty acid monoglyceride, polyglycerin polyricinolate, decaglycerin oleate, decaglycerin laurate, propylene glycol monooleate, coconut oil/rape seed oil (1:2) (transesterification), coconut oil/sunflower oil (1:3) (transesterification), palm oil, palm kernel oil, safflower oil, polyoxyethylene (20-80) sorbitan, glycerin trilaurate/glycerin trioleate (1:1), glycerin trioleate, n-capric acid, oleic acid, isostearic acid, sorbitan, soybean oil fatty acid methyl ester, and sucrose fatty acid ester.
5. The repellent of the above item 1 or 2 wherein the harmful flying insects are aphids.
6. The repellent of the above item 5 wherein the effective ingredient is at least one member selected from the following compounds:
   glycerin monocaprylate, glycerin monooleate, glycerin mono/dioleate, sorbitan laurate, sorbitan oleate, sorbitan palmitate, glycerin diacetomonolaurate, diacetyl tartaric acid saturated fatty acid monoglyceride, citric acid unsaturated fatty acid monoglyceride, succinic acid saturated fatty acid monoglyceride, tetraglycerin oleate, hexaglycerin laurate, decaglycerin oleate, decaglycerin laurate, poly (2-3) glycerin oleate, propylene glycol monooleate, coconut oil/rape seed oil (1:2) (transesterification), coconut oil/sunflower oil (1:3) (transesterification), coconut oil, palm oil, palm kernel oil, safflower oil, polyoxyethylene (40-60) sorbitan, glycerin trilaurate/glycerin trioleate (1:1), glycerin trioleate, n-capric acid, oleic acid, isostearic acid, sorbitan, soybean oil fatty acid methyl ester, and sucrose fatty acid ester.
7. The repellent of the above item 1 or 2 wherein the harmful flying insects are thrips.
8. The repellent of the above item 7 wherein the effective ingredient is at least one member selected from the following compounds:
   glycerin monocaprate, glycerin monolaurate, glycerin monostearate, glycerin monopalmitate, glycerin mono-12-hydroxy stearate, glycerin mono/dioleate, glycerin di/trioleate, diglycerin monostearate, diglycerin monolaurate, poly (2-3) glycerin oleate, tetraglycerin oleate, decaglycerin oleate, decaglycerin stearate, glycerin monoacetomonostearate, succinic acid saturated fatty acid monoglyceride, citric acid unsaturated fatty acid monoglyceride, diacetyl tartaric acid saturated fatty acid monoglyceride, sorbitan laurate, sorbitan palmitate, sorbitan trioleate, sorbitan stearate, sorbitol stearate, propylene glycol monooleate, polyoxyethylene (20-40) sorbitan, coconut oil/rape seed oil (1:2), coconut oil/sunflower oil (1:3), coconut oil/safflower oil (1:3), palm oil, coconut oil, glycerin trilaurate/glycerin trioleate (2:1), glycerin trilaurate/glycerin trioleate (1:1), glycerin trilaurate/glycerin trioleate (1:2), glycerin trilaurate/glycerin trimyristate (2:1), glycerin trilaurate/glycerin tripalmitate (2:1), glycerin trilaurate, sorbitol, sucrose oleate, sucrose laurate, and oleic acid.
9. A method for repelling flying insects harmful to a host plant which comprises providing a repellent of any one of the above items 1 to 8 and applying the repellent to the plant.

10. A method for repelling flying insects harmful to a host plant in a field which comprises providing a repellent of any one of the above items 1 to 8 and applying the repellent to the plant, wherein an area in which the repellent is not applied is provided in the field.

11. The method of the above item 10 wherein an attractant for the harmful flying insects and/or an insecticide and/or an adhesive for capturing the harmful flying insects is applied to the area in which the repellent is not applied.

12. The method of the above item 10 or 11 wherein a plant which is different from the host plant and more attractive to the harmful flying insects than the host plant is grown in the area in which the repellent is not applied.

13. The method of the above item 10 or 11 or 12 wherein an attractive tape for the harmful flying insects is provided in the area in which the repellent is not applied and/or the area in which the repellent is applied.

The repellent of the present invention can be in advance applied to a host plant to inhibit that adult harmful flying insects come flying, lay eggs and proliferate and to prevent or alleviate a potential damage by the harmful flying insects. In addition, it is possible to inhibit that virus-carrying harmful flying insects come flying and to prevent or alleviate generation of a potential viral disease. Further, the ingredient of the repellent of the present invention is very low toxic to human and animals and can be applied safely to agricultural products, fruit vegetables, fruit trees, flowers and ornamental plants.

BEST MODES FOR CARRYING OUT THE INVENTION

The ingredient of the repellent of the present invention is at least one member selected from glycerin fatty acid ester, sorbitan fatty acid ester, polyglycerin fatty acid ester, propylene glycol fatty acid ester, higher alcohol fatty acid ester, ethylene oxide adduct, polyoxyethylene sorbitan, fatty acid, sucrose fatty acid ester, sorbitan, and soybean oil fatty acid methyl ester. The fatty acids and the fatty acid components in the fatty acid esters are saturated or unsaturated, linear or branched or cyclic fatty acid having preferably 8-24 carbon atoms, more preferably 12-18 carbon atoms.

Specific examples of glycerin fatty acid esters include glycerin monofatty acid esters (for example, glycerin monopalmitate, glycerin monostearate, glycerin monooleate, glycerin monolinoleate, glycerin monobehenate, glycerin mono-12-hydroxy stearate, glycerin monocaprylate, glycerin monocaprate, glycerin monolaurate), glycerin mono/di fatty acid esters (for example, glycerin mono/dipalmitate, glycerin mono/distearate, glycerin mono/dioleate, glycerin mono/dilinoleate, glycerin mono/dibehenate, glycerin mono/di-12-hydroxy stearate), glycerin di/trifatty acid esters (for example, glycerin mono/tristearate, glycerin mono/trioleate), acetylated monoglycerides (for example, glycerin diacetomonolaurate, glycerin diacetomonostearate, glycerin diacetomonooleate, glycerin monoacetomonostearate), organic acid monoglycerides (for example, succinic acid saturated fatty acid monoglyceride, citric acid saturated fatty acid monoglyceride, citric acid unsaturated fatty acid monoglyceride, diacetyl tartaric acid saturated fatty acid monoglyceride, diacetyltartaric acid unsaturated fatty acid monoglyceride, lactic acid saturated fatty acid monoglyceride), polyglycerin fatty acid ester, fats and oils (glycerin trifatty acid esters), and synthetic fats and oils (glycerin trifatty acid esters).

Specific examples of sorbitan fatty acid esters include sorbitan laurate, sorbitan palmitate, sorbitan stearate, sorbitan tristearate, sorbitan oleate, sorbitan trioleate, sorbitan behenate, and sorbitan tribehenate.

Specific examples of polyglycerin fatty acid esters include diglycerin fatty acid esters (for example, diglycerin laurate, diglycerin stearate, diglycerin oleate, diglycerin caprylate, diglycerin monolaurate, diglycerin monostearate, diglycerin monooleate), polyglycerin fatty acid esters (for example, tetraglycerin stearate, tetraglycerin oleate, hexaglycerin laurate, hexaglycerin oleate, decaglycerin laurate, decaglycerin stearate), polyglycerin fatty acid esters (for example, tetraglycerin stearate, tetraglycerin oleate, hexaglycerin laurate, hexaglycerin oleate, decaglycerin laurate, decaglycerin stearate, decaglycerin oleate, polyglycerin polyricinolate).

Specific examples of propylene glycol fatty acid esters include propylene glycol monolaurate, propylene glycol monopalmitate, propylene glycol monostearate, propylene glycol monooleate, propylene glycol monobehenate, specific examples of higher alcohol fatty acid esters include stearylstearate, specific examples of ethylene oxide adducts include polyoxyethylene sorbitan monooleate, polyoxyethylene sorbitan trioleate, polyoxyethylene glycerin monostearate, polyoxyethylene glycerin monooleate. The number of added ethylene oxide is preferably 10-100 moles, more preferably 20-80 moles.

Specific examples of fatty acids include n-capric acid, oleic acid, isostearic acid, specific examples of sucrose fatty acid esters include oleate, and laurate, specific examples of sorbitans include sorbitol.

Examples of particularly preferred effective ingredient of the repellent to whiteflies include glycerin monofatty acid esters (for example, glycerin monocaprylate, glycerin mono-12-hydroxy stearate, glycerin monooleate), glycerin mono/difatty acid esters (for example, glycerin mono/dioleate), sorbitan fatty acid esters (for example, sorbitan laurate, sorbitan oleate, sorbitan trioleate), acetylated monoglycerides (for example, glycerin diacetomonolaurate), organic acid monoglycerides (for example, citric acid unsaturated fatty acid monoglyceride, succinic acid saturated fatty acid monoglyceride), polyglycerin fatty acid esters (for example, polyglycerin polyricinolate, decaglycerin oleate, decaglycerin laurate), propylene glycol fatty acid esters (for example, propylene glycol monooleate), fats and oils (for example, coconut oil/rape seed oil (1:2) (transesterification), coconut oil/sunflower oil (1:3) (transesterification), palm oil, palm kernel oil, safflower oil), polyoxyethylene (20-80) sorbitans (or example, polyoxyethylene (20) sorbitan, polyoxyethylene (40) sorbitan, polyoxyethylene (60) sorbitan, polyoxyethylene (80) sorbitan), synthetic fats and oils (for example, glycerin trilaurate/glycerin trioleate (1:1), glycerin trioleate), fatty acids (for example, n-capric acid, oleic acid, isostearic acid), sorbitan, soybean oil fatty acid methyl ester, and sucrose fatty acid esters.

Examples of particularly preferred effective ingredient of the repellent to aphids include glycerin monofatty acid esters (for example, glycerin monocaprylate, glycerin monooleate), glycerin mono/difatty acid esters (for example, glycerin mono/dioleate), sorbitan fatty acid esters (for example, sorbitan laurate, sorbitan oleate, sorbitan palmitate), acetylated monoglycerides (for example, glycerin diacetomonolaurate), organic acid monoglycerides (for example, diacetyl tartaric acid saturated fatty acid monoglyceride, citric acid unsaturated fatty acid monoglyceride, succinic acid saturated fatty acid monoglyceride), polyglycerin fatty acid esters (for example, tetraglycerin oleate, hexaglycerin laurate, decaglycerin oleate, decaglycerin laurate, poly (2-3) glycerin oleate), propylene glycol fatty acid esters (for example, propylene glycol monooleate), fats and oils (for example, coconut oil/rape seed oil (1:2) (transesterification), coconut oil/sunflower oil (1:3) (transesterification), coconut oil, palm oil, palm kernel oil, safflower oil), polyoxyethylene (20-80) sorbitans (for example, polyoxyethylene (40) sorbitan, polyoxyethylene (60) sorbitan), synthetic fats and oils (for example, glycerin trilaurate/glycerin trioleate (1:1), glycerin trioleate), fatty acids (for example, n-capric acid, oleic acid, isostearic acid), sorbitan, soybean oil fatty acid methyl ester, and sucrose fatty acid esters.

Examples of particularly preferred effective ingredient of the repellent to thrips include glycerin monofatty acid esters (for example, glycerin monocaprate, glycerin monolaurate, glycerin monostearate, glycerin monopalmitate, glycerin mono-12-hydroxy stearate), glycerin mono/difatty acid esters (for example, glycerin mono/dioleate), glycerin di/trifatty acid esters (for example, glycerin di/trioleate), diglycerin fatty acid esters (for example, diglycerin monostearate, diglycerin monolaurate), polyglycerin fatty acid esters (for example, poly (2-3) glycerin oleate, tetraglycerin oleate, decaglycerin oleate, decaglycerin stearate), acetylated monoglycerides (for example, glycerin monoacetomonostearate), organic acid monoglycerides (for example, succinic acid saturated fatty acid monoglyceride, citric acid unsaturated fatty acid monoglyceride, diacetyl tartaric acid saturated fatty acid monoglyceride), sorbitan fatty acid esters (for example, sorbitan laurate, sorbitan palmitate, sorbitan trioleate, sorbitan stearate, sorbitol stearate, propylene glycol fatty acid esters (for example, propylene glycol monooleate), polyoxyethylene (20-80) sorbitans (for example, polyoxyethylene (20) sorbitan, polyoxyethylene (40) sorbitan), triglycerides (fats and oils) (for example, transesterification oil, for example, coconut oil/rape seed oil (1:2), coconut oil/sunflower oil (1:3), coconut oil/safflower oil (1:3); fats and oils, for example, palm oil, coconut oil; synthetic fats and oils, for example, glycerin trilaurate/glycerin trioleate (2:1), glycerin trilaurate/glycerin trioleate (1:1), glycerin trilaurate/glycerin trioleate (1:2), glycerin trilaurate/glycerin trimyristate (2:1), glycerin trilaurate/glycerin tripalmitate (2:1), glycerin trilaurate), sorbitans (for example, sorbitol), sucrose fatty acid esters (for example, sucrose oleate, sucrose laurate), and fatty acids (for example, oleic acid).

The repellent of the present invention repels effectively plant harmful insects to protect the plant from the insects damage. Plant harmful insects to which the repellent of the present invention shows particularly the repelling effect include harmful flying insects (in particular, those which belong to Thysanoptera, Hemiptera (Heteroptera, Homoptera), Trichoptera, Lepidoptera, Coleoptera, Hymenoptera, and Diptera) and adult insects are targets.

Specific examples of harmful flying insects which is a target insect of the repellent of the present invention include Aleyrodidae (for example, greenhouse whitefly, silverleaf whitefly, sweetpotato whitefly, trialeurodes packardi), Aphidoidea (for example, cotton aphid, green peach aphid, Macrosiphoniella sanborni (Gillette), Aulacorthum solani (Kaltenbach), Macrosiphum euphorbiae (Thomas), Sitobion ibarae (Matsumura), Semiaphis heraclei (Takahashi), Neotoxoptera formosana (Takahashi), Rhodobium porosum (Sanderson), Aphis craccivora, Aphis forbesi (Weed), Chaetosiphon minor (Forbes), Rhopalosiphum rufiabdominalis (SASAKI)), Thripidae (for example, Thrips palmi (KARNY), Western Flower Thrips, Thrips tabaci (Lindeman), Thrips simplex, Scirtothrips dorsalis (Hood), Frankliniella intonsa (Trybom)), Phlaeothripidae, Yponomeutidae (for example, Plutella xylostella (Linnaeus, 1758)), Agromyzidae (for example, Serpentine leafminer, Liriomyze trifolii (BURGESS), Liriomyza sativae (BLANCHARD), Liriomyza bryoniae (KALTENBACH), Phytomyza horticola (GOUREA), Liriomyza dianthicola(Venturi)), Pyralidae (for example, Diaphania indica (Saunder), Diaphania indica (Saunders)), Noctuidae (for example, Spodoptera litura (Fabricius), Spodoptera exigua (Hubner), Helicoverpa armigera (Hubner), Helicoverpa assulta (Guenee), Spodoptera depravata (Butler), Pieris rapae, Taylorilygus apicalis (Fieber) to which the present invention is not limited.

Plants to which the repellent of the present invention is applied are those to be damaged by harmful flying insects and typical examples of such plants include Cucurbitaceae (for example, cucumber, melon, water melon, pumpkin, Cucumis melo var. conomon, oriental melon, sponge gourd, bittercucumber), Solanaceae (for example, tomato, eggplant, sweet pepper, petunia, Solanum photeinocarpum Naka. et Oda., potato), Leguminosae (for example, common bean, broad bean, azuki bean, soybean, asparagus bean, string bean), Asteraceae (for example, tagetes, Arctium lappa L, Chrysanthemum coronarium, ettuce, chrysanthemum, transvaal daisy, cineraria), Brassicaceae (for example, chinese cabbage, cabbage, daikon, turnip, komatsuna, broccoli, qing geng cai, stock), Malvaceae (for example, okra)), Apiaceae (for example, celery, carrot, parsley), edaliaceae (for example, sesame), Liliaceae (for example, onion, chinese chive, asparagus, scallion), Caryophyllaceae (for example, gypsophila, carnation), Rutaceae (for example, citrus), Rosaceae (for example, rose, strawberry, apple, pear, pear (Europian pear), peach, nectarine), Vitaceae (for example, grape), Lamiaceae (for example, beefsteak plant), Malvaceae (for example, cotton), Chenopodiaceae (for example, spinach), Gentianaceae (for example, Eustoma russellianum), Violaceae (for example, pansy), Primulaceae (for example, cyclamen), Ranunculaceae (for example, clematis), and Euphorbiaceae (for example, poinsettia) to which the present invention is not limited.

The repellent of the present invention may consist of the effective ingredient mentioned above alone or may contain auxiliaries including polyoxyalkylene nonionic surfactants such as polyoxyethylene monoalkyl ether, polyoxyethylene monoaryl ether.

Specific examples of auxiliaries include polyoxyethylene (5) monododecyl ether, and diglycerin monooleate: (polyoxyethylene phenyl ether+dodecylbenzenesulfonate): soybean oil (1:1:1).

The content of the auxiliaries is preferably 5 to 70 parts by mass, more preferably 20 to 50 parts by mass per 100 parts by mass of the effective ingredient.

The repellent of the present invention may be formulated including other auxiliaries such as conventional surfactants and talc. An application form of the repellent of the invention is not limited to specific ones but may be, for example, wettable powder, emulsifiable concentrate, powder, and flowable. The repellent of the present invention may further comprise insecticides, microbicides, plant growth regulants, and etc.

In addition to nonionic surfactants for formulating the repellent, it is possible to use conventional surfactants for formulation such as cationic surfactants, anionic surfactants, amphoteric surfactants, and etc.

The present invention also provides a method for repelling harmful flying insects to a host plant which comprises the step of applying the repellent of the present invention to the host plant. The repellent of the present invention is diluted with water to preferably 0.05 to 5% by mass, more preferably 0.2 to 0.5% by mass and applied to a host plant in the amount of preferably 0.2 kg/10a to 8 kg/10a, more preferably 0.5 kg/10a to 3 kg/10a. The repellent is applied preferably before harmful flying insects come flying but is effective even after harmful flying insects come flying.

The present invention further provides a method for repelling flying insects harmful to a host plant in a field which comprises the steps of providing the repellent of the present invention and applying the repellent to the plant, wherein an area in which the repellent is not applied is provided in the field. The area in which the repellent is not applied means those where the repellent is substantially ineffective, for example, such area is provided preferably around an inlet of the field or ventilating opening of the field.

Examples of more specific methods include a method wherein an attractant for the harmful flying insects and/or an insecticide and/or an adhesive for capturing the harmful flying insects is applied to the area in which the repellent is not applied, a method wherein a plant which is different from the host plant and more attractive to the harmful flying insects than the host plant is grown in the area in which the repellent is not applied, and a method wherein an attractive tape for the harmful flying insects is provided in the area in which the repellent is not applied.

In case of the method wherein an area in which the repellent is not applied is provided in the field, the number and the surface area of the area depend on a host plant and target harmful flying insects but suitably are 5 to 10 plots per 5 to 10a of the field and about 1 to 5 m² per each plot. Coverage of attractants and/or insecticides and/or adhesives for capturing the harmful flying insects applied to the area to which the repellent is not applied is conventional one, for example, 0.2 to 6 kg/10a, preferably 0.1 to 2 kg/10a of the non-applied area. Attractants and insecticides are not limited to specific ones. Adhesives for capturing the harmful flying insects are not limited to specific ones, and include synthetic rubber adhesives and acrylic resin adhesives. Commercially available ones include "Kinryu Spray" available from Maruzen Chemical. Spray type adhesive may also be used. The adhesive is thoroughly sprayed onto a host plant which is then cultivated as it is. Insects such as whiteflies that come into contact with the plant are captured by the adhesive. If the adhesive is not sprayed, insects may fly apart from the plant by wind or on contact with human but they are surely captured by the adhesive sprayed plant and never fly apart. Since the adhesives themselves do not have any repelling effect, insects such as whiteflies come flying onto the adhesives likewise plants to which the adhesives are not sprayed.

A different plant that is to be grown in the area to which the repellent is not applied and is more attractive to target harmful flying insects than a host plant depends on the kinds of the host plant and the target harmful flying insect. For example, in case of whitefly (in particular, silverleaf whitefly), if a host plant is tomato, the different plant is cucumber, common bean, etc., in case of aphid (in particular, cotton aphid), if a host plant is green pepper, the different plant is eggplant, cucumber, etc., and in case of thrips (in particular, thrips palmi Karny), if a host plant is strawberry, the different plant is cucumber, common bean, etc.

When an attractive tape for the harmful flying insects is provided in the area to which the repellent is not applied and/or the area to which the repellent is applied, the tape is preferably colored one and the color depends on the target harmful flying insects. For example, yellow color tape is for whitefly and aphid and blue or white color tape is for thrips. For example, commercially available attractive paper such as "Kinryu" is yellow or blue paper on which a paste (adhesive for capturing) has been sprayed. Material, width, length and thickness of the tape are suitably determined, for example, it is effective that a plastic or paper tape having width of 50 to 500 mm, length of 100 to 700 mm, and thickness of 0.1 to 0.5 mm is provided in the amount of the total surface area of the tape of about 1 to 20 m² per 10a of the area in which the repellent is applied or not applied.

EXAMPLES

Example 1

Main ingredients (80 parts by mass) and auxiliary A (polyoxyethylene (5) monododecyl ether) (20 parts by mass) listed in Table 1 were mixed to prepare a sample of the repellent of the present invention.

The repellent was diluted with water to 200 mg/100 ml which was then applied to seed leaves of common bean (variety: Taisho Kintoki). As control samples, auxiliary A alone and distilled water were used. After drying, the plant was maintained at 22 to 30° C. for 3 days in an isolated room in which adult greenhouse whiteflies were grown and the number of adult insects that came flying was counted with time. A repelling ratio was determined according to the following formula.

Repelling ratio (%)=100×[1−(the number of adult insects in the repellent applied area)/(the number of adult insects in the distilled water applied area)]

Results are shown in Table 1.

TABLE 1

Repelling effects of the samples to greenhouse whitefly

| No. | Effective ingredients | Repelling ratio (%) |
|---|---|---|
| 1-1 | glycerin monocaprylate | 82 |
| 1-2 | glycerin monooleate | 82 |
| 1-3 | glycerin mono/dioleate | 93 |
| 1-4 | sorbitan laurate | 92 |
| 1-5 | sorbitan oleate | 80 |
| 1-6 | glycerin diacetomonolaurate | 96 |
| 1-7 | citric acid unsaturated fatty acid monoglyceride | 73 |
| 1-8 | decaglycerin oleate | 76 |
| 1-9 | decaglycerin laurate | 80 |
| 1-10 | propylene glycol monooleate | 82 |
| 1-11 | coconut oil/rape seed oil (1:2) (transesterification) | 79 |
| 1-12 | coconut oil | 93 |
| 1-13 | palm kernel oil | 85 |
| 1-14 | safflower oil | 77 |
| 1-15 | polyoxyethylene (40) sorbitan | 70 |
| 1-16 | polyoxyethylene (60) sorbitan | 73 |
| 1-17 | glycerin trilaurate/glycerin trioleate (1:1) | 85 |
| 1-18 | n-capric acid | 90 |
| 1-19 | oleic acid | 84 |
| 1-20 | isostearic acid | 72 |
| 1-21 | sorbitan | 74 |
| 1-22 | soybean oil fatty acid methyl ester | 81 |
| 1-23 | auxiliary A | 5 |
| 1-24 | distilled water | 0 |

Example 2

Main ingredients (80 parts by mass) and auxiliary B (diglycerin monooleate: (polyoxyethylene phenyl ether+dodecylbenzenesulufonate): soybean oil (1:1:1) (20 parts by mass) listed in Table 2 were mixed to prepare a sample of the repellent of the present invention.

The repellent was diluted with water to 200 mg/100 ml which was then applied to seed leaves of cucumber (variety:

Sagami Hanjiro). As control samples, auxiliary B alone and distilled water were used. After drying, the plant was maintained at 22 to 30° C. for 3 days in an isolated room in which adult silverleaf whiteflies were grown and the number of adult insects that came flying was counted with time. A repelling ratio was determined according to the following formula.

Repelling ratio (%)=100×[1−(the number of adult insects in the repellent applied area)/(the number of adult insects in the distilled water applied area)]

Results are shown in Table 2.

TABLE 2

Repelling effects of the samples to silverleaf whitefly

| No. | Effective ingredients | Repelling ratio (%) |
|---|---|---|
| 2-1 | glycerin monocaprylate | 73 |
| 2-2 | glycerin monooleate | 70 |
| 2-3 | glycerin mono/dioleate | 95 |
| 2-4 | sorbitan laurate | 92 |
| 2-5 | sorbitan oleate | 75 |
| 2-6 | glycerin diacetomonolaurate | 94 |
| 2-7 | citric acid unsaturated fatty acid monoglyceride | 71 |
| 2-8 | decaglycerin oleate | 75 |
| 2-9 | decaglycerin laurate | 70 |
| 2-10 | propylene glycol monooleate | 73 |
| 2-11 | coconut oil/rape seed oil (1:2) (transesterification) | 76 |
| 2-12 | coconut oil | 91 |
| 2-13 | palm kernel oil | 83 |
| 2-14 | safilower oil | 71 |
| 2-15 | polyoxyethylene (40) sorbitan | 85 |
| 2-16 | polyoxyethylene (60) sorbitan | 77 |
| 2-17 | glycerin trilaurate/glycerin trioleate (1:1) | 88 |
| 2-18 | n-capric acid | 86 |
| 2-19 | oleic acid | 68 |
| 2-20 | isostearic acid | 65 |
| 2-21 | sorbitan | 67 |
| 2-22 | soybean oil fatty acid methyl ester | 63 |
| 2-23 | auxiliary B | 7 |
| 2-24 | distilled water | 0 |

Example 3

Main ingredients (80 parts by mass) and auxiliary A (polyoxyethylene (5) monododecyl ether) (20 parts by mass) listed in Table 3 were mixed to prepare a sample of the repellent of the present invention.

The repellent was diluted with water to 200 mg/100 ml which was then applied to true leaves of cucumber (variety: Sagami Hanjiro at 0.7 leaf stage). As control samples, auxiliary A alone and distilled water were used. After drying, the plant was maintained at 22 to 30° C. for 7 days in an isolated room in which cotton aphid were grown and the number of adult insects that came flying was counted with time. A repelling ratio was determined according to the following formula.

Repelling ratio (%)=100×[1−(the number of adult insects in the repellent applied area)/(the number of adult insects in the distilled water applied area)]

Results are shown in Table 3.

TABLE 3

Repelling effects of the samples to cotton aphid

| No. | Effective ingredients | Repelling ratio (%) |
|---|---|---|
| 3-1 | glycerin monocaprylate | 88 |
| 3-2 | glycerin monooleate | 85 |
| 3-3 | glycerin mono/dioleate | 92 |
| 3-4 | sorbitan laurate | 96 |
| 3-5 | sorbitan oleate | 93 |
| 3-6 | glycerin diacetomonolaurate | 82 |
| 3-7 | citric acid unsaturated fatty acid monoglyceride | 92 |
| 3-8 | decaglycerin oleate | 95 |
| 3-9 | decaglycerin laurate | 90 |
| 3-10 | propylene glycol monooleate | 82 |
| 3-11 | coconut oil/rape seed oil (1:2) (transesterification) | 88 |
| 3-12 | palm oil | 76 |
| 3-13 | safflower oil | 78 |
| 3-14 | polyoxyethylene (40) sorbitan | 75 |
| 3-15 | polyoxyethylene (60) sorbitan | 78 |
| 3-16 | glycerin trilaurate/glycerin trioleate (1:1) | 88 |
| 3-17 | n-capric acid | 76 |
| 3-18 | oleic acid | 70 |
| 3-19 | sorbitan | 68 |
| 3-20 | auxiliary A | 3 |
| 3-21 | distilled water | 0 |

Example 4

Main ingredients (80 parts by mass) and auxiliary B (diglycerin monooleate: (polyoxyethylene phenyl ether+dodecylbenzenesulufonate): soybean oil (1:1:1)) (20 parts by mass) listed in Table 4 were mixed to prepare a sample of the repellent of the present invention.

The repellent was diluted with water to 200 mg/100 ml which was then applied to seed leaves of eggplant (variety: Senryo No. 2). As control samples, auxiliary B alone and distilled water were used. After drying, the plant was maintained at 22 to 30° C. for 7 days in an isolated room in which green peach aphid were grown and the number of adult insects that came flying was counted with time. A repelling ratio was determined according to the following formula.

Repelling ratio (%)=100×[1−(the number of adult insects in the repellent applied area)/(the number of adult insects in the distilled water applied area)]

Results are shown in Table 4.

TABLE 4

Repelling effects of the samples to green peach aphid

| No. | Effective ingredients | Repelling ratio (%) |
|---|---|---|
| 4-1 | glycerin monocaprylate | 76 |
| 4-2 | glycerin monooleate | 81 |
| 4-3 | glycerin mono/dioleate | 88 |
| 4-4 | sorbitan laurate | 82 |
| 4-5 | sorbitan oleate | 85 |
| 4-6 | glycerin diacetomonolaurate | 77 |
| 4-7 | citric acid unsaturated fatty acid monoglyceride | 81 |
| 4-8 | decaglycerin oleate | 78 |
| 4-9 | decaglycerin laurate | 83 |
| 4-10 | propylene glycol monooleate | 76 |
| 4-11 | coconut oil/rape seed oil (1:2) (transesterification) | 81 |
| 4-12 | palm oil | 77 |
| 4-13 | safflower oil | 68 |
| 4-14 | polyoxyethylene (40) sorbitan | 82 |
| 4-15 | polyoxyethylene (60) sorbitan | 80 |

TABLE 4-continued

Repelling effects of the samples to green peach aphid

| No. | Effective ingredients | Repelling ratio (%) |
|---|---|---|
| 4-16 | glycerin trilaurate/glycerin trioleate (1:1) | 86 |
| 4-17 | n-capric acid | 68 |
| 4-18 | oleic acid | 70 |
| 4-19 | sorbitan | 62 |
| 4-20 | auxiliary B | 5 |
| 4-21 | distilled water | 0 |

Example 5

Main ingredients (80 parts by mass) and auxiliary A (polyoxyethylene (5) monododecyl ether) (20 parts by mass) listed in Table 5 were mixed to prepare a sample of the repellent of the present invention.

The repellent was diluted with water to 200 mg/100 ml which was then applied to true leaves of eggplant (variety: Senryo No. 2 at 3.5 leaf stage). As control samples, auxiliary A alone and distilled water were used. After drying, the plant was maintained at 22 to 30° C. for 10 days in an isolated room in which adult western flower thrips were grown and the degree of insect damage (the number of insect damage spots) was observed and were totaled based on the criteria: 0 for no damage, 1 for very slight damage, 3 for slight damage, 5 for remarkable damage and 10 for serious damage. A repelling ratio was determined according to the following formula.

Repelling ratio (%)=100×[1−(the total degree of insect damage in the repellent applied area)/(the total degree of insect damage in the distilled water applied area)]

Results are shown in Table 5.

TABLE 5

Repelling effects of the samples to western flower thrips

| No. | Effective ingredients | Repelling ratio (%) |
|---|---|---|
| 5-1 | glycerin monolaurate | 62 |
| 5-2 | glycerin monostearate | 58 |
| 5-3 | glycerin monopalmitate | 68 |
| 5-4 | glycerin mono/dioleate | 82 |
| 5-5 | diglycerin monostearate | 60 |
| 5-6 | poly (2-3) glycerin oleate | 58 |
| 5-7 | decaglycerin stearate | 77 |
| 5-8 | glycerin monoacetomonostearate | 68 |
| 5-9 | succinic acid saturated acid monoglyceride | 70 |
| 5-10 | sorbitan laurate | 53 |
| 5-11 | sorbitan palmitate | 72 |
| 5-12 | propylene glycol monooleate | 80 |
| 5-13 | polyoxyethylene (20) sorbitan | 68 |
| 5-14 | polyoxyethylene (40) sorbitan | 75 |
| 5-15 | coconut oil/rape seed oil (1:2) | 66 |
| 5-16 | coconut oil/sunflower oil (1:3) | 71 |
| 5-17 | palm oil | 68 |
| 5-18 | coconut oil | 82 |
| 5-19 | glycerin trilaurate/glycerin trioleate (1:2) | 58 |
| 5-20 | glycerin trilaurate/glycerin trimyristate (2:1) | 80 |
| 5-21 | glycerin trilaurate/glycerin tripalmitate (1:1) | 75 |
| 5-22 | glycerin trilaurate | 82 |
| 5-23 | sorbitol | 61 |
| 5-24 | sucrose fatty acid ester (oleate) | 58 |
| 5-25 | sucrose fatty acid ester (laurate) | 55 |
| 5-26 | oleic acid | 76 |
| 5-27 | auxiliary A | 8 |
| 5-28 | distilled water | 0 |

Example 6

The same procedures in Example 5 were repeated to prepare the repellent except that auxiliary B (diglycerin monooleate : (polyoxyethylene phenyl ether+dodecylbenzenesulufonate): soybean oil (1:1:1)) was used in place of auxiliary A.

The repellent was diluted with water to 200 mg/100 ml which was then applied to true leaves of eggplant (variety: Senryo No. 2 at 3.5 leaf stage). As control samples, auxiliary B alone and distilled water were used. After drying, the plant was maintained at 22 to 30° C. for 10 days in an isolated room in which adult Thrips palmi Karny were grown and the degree of insect damage (the number of insect damage spots) was observed and were totaled based on the criteria: 0 for no damage, 1 for very slight damage, 3 for slight damage, 5 for remarkable damage and 10 for serious damage. A repelling ratio was determined according to the following formula.

Repelling ratio (%)=100×[1−(the total degree of insect damage in the repellent applied area)/(the total degree of insect damage in the distilled water applied area)]

Results are shown in Table 6.

TABLE 6

Repelling effects of the samples to Thrips palmi Karny

| No. | Effective ingredients | Repelling ratio (%) |
|---|---|---|
| 6-1 | glycerin monolaurate | 65 |
| 6-2 | glycerin monostearate | 62 |
| 6-3 | glycerin monopalmitate | 71 |
| 6-4 | glycerin mono/dioleate | 83 |
| 6-5 | diglycerin monostearate | 55 |
| 6-6 | poly (2-3) glycerin oleate | 68 |
| 6-7 | decaglycerin stearate | 70 |
| 6-8 | glycerin monoacetomonostearate | 55 |
| 6-9 | succinic acid saturated acid monoglyceride | 71 |
| 6-10 | sorbitan laurate | 63 |
| 6-11 | sorbitan palmitate | 73 |
| 6-12 | propylene glycol monooleate | 81 |
| 6-13 | polyoxyethylene (20) sorbitan | 54 |
| 6-14 | polyoxyethylene (40) sorbitan | 69 |
| 6-15 | coconut oil/rape seed oil (1:2) | 56 |
| 6-16 | coconut oil/sunflower oil (1:3) | 85 |
| 6-17 | palm oil | 56 |
| 6-18 | coconut oil | 85 |
| 6-19 | glycerin trilaurate/glycerin trioleate (1:2) | 76 |
| 6-20 | glycerin trilaurate/glycerin trimyristate (2:1) | 83 |
| 6-21 | glycerin trilaurate/glycerin tripalmitate (1:1) | 78 |
| 6-22 | glycerin trilaurate | 90 |
| 6-23 | sorbitol | 55 |
| 6-24 | sucrose fatty acid ester (oleate) | 62 |
| 6-25 | sucrose fatty acid ester (laurate) | 68 |
| 6-26 | oleic acid | 69 |
| 6-27 | auxiliary B | 9 |
| 6-28 | distilled water | 0 |

What is claimed is:

1. A method for repelling flying insects harmful to a host plant which comprises applying a repellent to the plant before said harmful insects come to the plant to inhibit said harmful insect from coming to the plant,
    wherein said repellent comprises,
        as an effective ingredient, at least one member selected from the group consisting of glycerin diacetomonolaurate, and a mixture of glycerin monooleate and glycerin dioleate, and
        an auxiliary agent comprising diglycerin monooleate, a mixture of polyoxyethylene phenyl ether and dodecylbenzenesulfonate, and soybean oil; and
    wherein said insects are adult whiteflies.

2. The method of claim 1, wherein the repellent is applied to only a fraction of a field.

3. The method of claim 2, wherein an attractant for the harmful flying insects and/or an insecticide and/or an adhesive for capturing the harmful flying insects is applied to the area in which the repellent is not applied.

4. The method of claim 2, wherein a plant which is a different species from the host plant and which has properties which make the plant itself more attractive to the harmful flying insects than the host plant is grown in the area in which the repellent is not applied.

5. The method of claim 2, wherein an attractive tape for the harmful flying insects is provided in the area in which the repellent is not applied and/or the area in which the repellent is applied.

6. The method of claim 1, wherein the effective ingredient is glycerin diacetomonolaurate.

7. The method of claim 1, further comprising applying at least one of an attractant for the harmful flying insects, an insecticide, and an adhesive for capturing the harmful flying insects to the area in which the repellent is not applied.

8. The method of claim 1, further comprising growing a plant which is a different species from the host plant and which has properties which make the plant itself more attractive to the harmful flying insects than the host plant in the area in which the repellent is not applied.

9. The method according to claim 1, further comprising diluting said repellent with water so that the concentration of said repellent is within a range of 0.05 to 5% by mass.

10. The method according to claim 9, further comprising applying the diluted repellent to said host plant in an amount of from 0.2 kg/10 a to 8 kg/10 a.

11. The method of claim 1, wherein the effective ingredient is a mixture of glycerin monooleate and glycerin dioleate.

12. The method according to claim 1, wherein
a mass ratio of diglycerin monooleate: a mixture of polyoxyethylene phenyl ether and dodecylbenzenesulfonate: soybean oil is 1:1:1.

13. The method according to claim 1, wherein said auxiliary agent is present in said repellent in an amount of from 5 to 70 parts by mass per 100 parts by mass of said effective ingredient.

* * * * *